United States Patent [19]

Chu et al.

[11] Patent Number: 4,694,114

[45] Date of Patent: Sep. 15, 1987

[54] PROCESS FOR ISOMERIZING ALKYL AROMATIC HYDROCARBONS UTILIZING ZSM-23 ZEOLITE AND A HYDROGENATION/DEHYDROGENATION METAL

[75] Inventors: Yung-Feng Chu, Cherry Hill, N.J.; James C. Vartuli, West Chester, Pa.

[73] Assignee: Mobil Oil Corporation, New York, N.Y.

[21] Appl. No.: 885,319

[22] Filed: Jul. 14, 1986

Related U.S. Application Data

[63] Continuation of Ser. No. 766,687, Aug. 19, 1985, abandoned, which is a continuation of Ser. No. 569,827, Jan. 11, 1984, abandoned.

[51] Int. Cl.$^4$ ................................................ C07C 5/22
[52] U.S. Cl. .................................................... 585/481
[58] Field of Search ......................................... 585/481

[56] References Cited

U.S. PATENT DOCUMENTS

| | | | |
|---|---|---|---|
| 4,104,151 | 8/1978 | Rubin et al. | 208/111 |
| 4,128,591 | 12/1978 | Carr et al. | 260/668 |
| 4,385,195 | 5/1983 | Butter et al. | 585/481 |

*Primary Examiner*—Curtis R. Davis
*Attorney, Agent, or Firm*—A. J. McKillop; M. G. Gilman; M. V. Schneller

[57] ABSTRACT

Alkyl aromatic hydrocarbons including ethyl benzene are isomerized to xylenes utilizing a catalyst consisting essentially of ZSM-23 zeolite, platinum (or other metal such as palladium, nickel, gold, zinc, or gallium) and an alumina support.

6 Claims, No Drawings

PROCESS FOR ISOMERIZING ALKYL AROMATIC HYDROCARBONS UTILIZING ZSM-23 ZEOLITE AND A HYDROGENATION/DEHYDROGENATION METAL

This is a continuation of copending application Ser. No. 766,687, filed on Aug. 19, 1985 now abandoned, which is a continuation of Ser. No. 569,827, filed Jan. 11, 1984, now abandoned.

BACKGROUND OF THE INVENTION

This invention relates in general to a catalyst and process for the isomerization of alkyl aromatics. In particular, the invention relates to improvements in the commercial processes in which a mixture of xylenes and ethylbenzene are reacted along with hydrogen over a platinum-containing catalyst to produce a near equilibrium mixture of xylenes while converting ethylbenzene to xylenes.

Isomerization of alkyl aromatics has become particularly important commercially. In processes for the production of xylenes, the ortho and paraxylenes are the preferred products. Paraxylene is principally used in preparation of polyesters, while orthoxylene's main end use is in preparation of phthalic anhydride. Metaxylene has fewer important end uses and thus may be converted to the para and ortho forms, which have greater commercial value.

Ethylbenzene is difficult to separate from the xylenes since their boiling points are very close. Accordingly, ethylbenzene is normally present within the mixture of xylenes prepared by extraction or distillation from a hydrocarbon stream. Generally there are two approaches to the problem of processing the ethylbenzene in a mixed xylene stream. Because ethylbenzene is not easily isomerized one approach has been to destroy the ethylbenzene through disproportionation, hydrodealkylation or the like to yield lighter and heavier compounds which can be separated by distillation from the $C_8$ compounds. One drawback to this approach has been the accompanying loss of significant quantities of potential xylenes in this reaction.

It is also known in the prior art to react ethylbenzene to form xylenes in the presence of hydrogen and a hydrogenation-dehydrogenation catalyst, preferably platinum on alumina. U.S. Pat. No. 2,976,332 discloses a catalyst comprising platinum on alumina plus an amorphous silica/alumina to convert ethylbenzene and to isomerize xylenes with a minimum of side reactions which reduce the yield selectivity and contribute to catalyst aging.

Combination catalysts which are capable of isomerizing xylenes and ethylbenzenes to approach an equilibrium distribution of isomers include U.S. Pat. No. 2,976,332 which combines platinum on alumina with amorphous silica-alumina. Another combination catalyst is disclosed in U.S. Pat. No. 3,409,686 in which alumina gel is mixed with particles of hydrogen mordenite to form a mixed base which is subsequently dried and impregnated with a platinum solution. In U.S. Pat. No. 3,767,721 platinum on alumina in a fine powdered form is combined with powdered mordenite. Hydrogen mordenite in such a combination, however, is overly active and promotes destructive reactions which are undesirable. U.S. Pat. No. 4,128,591 discloses a catalyst and process for producing a near equilibrium mixture of xylene from a feedstream comprising ethylbenzene and mixed xylenes. The catalyst combines a platinum containing hydrogenation/dehydrogenation component on an alumina support with a form of hydrogen mordenite.

The prior art discloses a number of catalysts for isomerization of xylenes alone or combined with the conversion of ethylbenzenes to xylenes. While some of the prior art catalysts have been successful in isomerizing xylenes in ethylbenzene, further improvement has been desired in order to achieve a more selective catalyst which can be operated to approach chemical equilibrium in the isomerization of xylenes and ethylbenzene while at the same time avoiding the destructive reactions which can result in a loss of $C_8$ aromatics.

SUMMARY OF THE INVENTION

We have now discovered a new catalyst that may be used in producing an equilibrium mixture of xylenes from a feed comprising mainly ethylbenzene and mixed xylenes. The catalyst consists essentially of one or more metals selected from the group consisting of platinum, palladium, nickel, gold, zinc or gallium functioning as the hydrogenation-dehydrogenation component contained on or in alumina in combination with hydrogen ZSM-22 or hydrogen ZSM-23 zeolites. The metal can be contained on either the alumina or the zeolite or on both the alumina and zeolite, particularly if these have been combined in a pelletized or extrudate form.

DESCRIPTION OF THE INVENTION

Catalyst Composition

The catalyst of this invention is composed of three basic components: a support, hydrogenation-dehydrogenation metal contained on the support, and the hydrogen form of ZSM-22 or ZSM-23 zeolite. For the support, alumina is preferred.

Platinum alone may be used as the hydrogenation-dehydrogen component, although palladium, nickel, gold, zinc, gallium and rhenium or mixtures of these may be included. The usable range of metal in elemental form will be in the range of 0.5 to 1 weight percent of the finished catalyst. The preferred range of metal concentrations in the finished catalyst is, however, between 0.1 and 0.6 percent by weight. The amount used is determined, of course, by its effectiveness in the finished catalyst.

The metal, such as platinum, can be deposited on the alumina support by various methods, including adsorption by an alumina slurry in a solution of a water-soluble salt of platinum and absorption of said solutions by a dry powdered alumina. Alternatively the zeolite may be used to support the metal by ion exchanging or impregnation techniques. An extrudate made up of the zeolite and the alumina can be exchanged or impregnated with metal. The metal can also be incorporated into the zeolite during synthesis thereof. Following deposition of the metal, it can be usually fixed in place by treatment with hydrogen sulfide, reduction to elemental metallic form or oxidation by calcination.

The third ingredient of the catalyst of this invention is the ZSM-22 or ZSM-23 zeolite.

Zeolite ZSM-22 is the subject of pending applications, U.S. Ser. No. 373,452, U.S. Ser. Nos. 373,453, and 373,451, all filed on Apr. 30, 1982. Each of these applications is incorporated herein by reference.

The ZSM-22 highly siliceous zeolite can be suitably prepared from a reaction mixture containing a source of silica, $Q_2O$, an alkali metal oxide, e.g., sodium, potassium or cesium, water, and alumina, and having a composition, in terms of mole ratios of oxides, falling within the following ratios:

| Reactants | Broad | Preferred |
|---|---|---|
| $SiO_2/Al_2O_3 =$ | 20 to ∞ | 30 to 1000 |
| $M_{2/n}O/(Q_2O + M_{2/n}O) =$ | 0 to 0.95 | 0.1 to 0.8 | wherein $Q_2O$ is the oxide form of an organic compound of an element of Group 5-B of the Periodic Table, e.g., N, P, preferably N, containing at least one alkyl or aryl group having at least 2 carbon atoms, and M is an alkali or alkaline earth metal of valence n, and maintaining the mixture at crystallization temperature until crystals of the new ZSM-22 zeolite are formed. Thereafter, the crystals are separated from the liquid by any conventional means, washed and recovered. The zeolite of this invention can be used in aromatics alkylation reactions (e.g., toluene alkylation by methanol and ethylene), toluene disproportionation, selective cracking of a meta/para-cymene mixture and in conversion of various oxygenates to gasoline-grade hydrocarbons and/or chemicals, e.g., olefins.

Crystallization can be carried out at either static or stirred conditions in a reactor vessel, e.g., a polypropylene jar, teflon lined or stainless steel autoclaves, at 80° C. (176° F.) to about 210° C. (410° F.) for about 6 hours to 150 days. Thereafter, the crystals are separated from the liquid and recovered. The composition can be prepared utilizing materials which supply the appropriate oxide. Such materials include aluminates, alumina, silicates, sodium silicate, silica hydrosol, silica gel, silicic acid, sodium, potassium or cesium hydroxide, and an organic compound. The organic compound contains an element of Group 5-B, such as nitrogen or phosphorus, preferably nitrogen. The preferred compounds are generally expressed by the following formula:

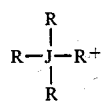

or $R_4J^+$ wherein J is an element of Group 5-B of the Periodic Table, e.g. N or P, preferably N, and each R is an alkyl or aryl group having at least two (2) carbon atoms or hydrogen. Suitable organic compounds are dialkylammonium compounds wherein each of the alkyl groups is the same or different and each alkyl group has two (2) to eight (8) carbon atoms, e.g., ethyl, propyl, butyl, pentyl, hexyl, heptyl or octyl. The reaction mixture can be prepared either batchwise or continuously. Crystal size and crystallization time of the new crystalline material will vary with the nature of the reaction mixture employed and the crystallization conditions.

The highly siliceous ZSM-22 zeolite comprises crystalline, three-dimensional continuous framework silicon-containing structures or crystals which result when all the oxygen atoms in the tetrahedra are mutually shared between tetrahedral atoms of silicon or aluminum, and which can exist with a network of mostly $SiO_2$, i.e. exclusive of any intracrystalline cations. Similar crystals form building blocks of materials, such as quartz, cristobalite and a long list of zeolite structures such as ZSM-5, ZSM-11, ZSM-12, ZSM-23, ZSM-35, ZSM-38, ZSM-48 (described in European Patent Application No. 80,300,463 published Sept. 3, 1980 as Publication No. 0,015,132, the entire content of which is incorporated herein by reference), mordenite and perhaps even faujasite. Not all zeolite structures are known to exist at this time in predominantly $SiO_2$-containing compositions—so the above class of materials does not presently include some zeolites, such as zeolite A.

The ZSM-22 zeolite also may contain a relatively minor amount of $Al_2O_3$ and therefore can produce a product with a $SiO_2$ to $Al_2O_3$ ratio of about 20 to about infinity. In the as-synthesized form, the ZSM-22 has a calculated composition, in terms of moles of oxides, after dehydration, per 100 moles of silica, as follows:

$(x)Q_2O:(y)M_{2/n}O:(z)L_2O_3:100SiO_2$ wherein $Q_2O$ is the oxide form of an organic compound containing an element of Group 5-B (as defined in the Table of the Elements—National Bureau of Standards, Fischer Scientific Co. Catalog No. 5-702-10) e.g., N or P, preferably N, containing at least one alkyl or aryl group having at least 2 carbon atoms, M is an alkali metal or an alkaline earth metal having a valence n, and wherein $x=0.01-2.0$, $y=0-2.0$, $z=0-5$, and $L=Al$.

ZSM-22 can further be identified by its sorptive characteristics and its X-ray diffraction pattern. The original cations of the as-synthesized ZSM-22 may be replaced at least in part by other ions using conventional ion exchange techniques. It may be necessary to precalcine the ZSM-22 zeolite crystals prior to ion exchange. The replacing ions introduced to replace the original alkali, alkaline earth and/or organic cations may be any that are desired so long as they can pass through the channels within the zeolite crystals. Desired replacing ions are those of hydrogen, rare earth metals, metals of Groups IB, IIA, IIB, IIIA, IIIB, IVA, IVB, VIB and VIII of the Periodic Table. Among the metals, those particularly preferred are rare earth metals, manganese, zinc and those of Group VIII of the Periodic Table.

ZSM-22 zeolite described herein has a definite X-ray diffraction pattern, set forth below in Table I, which distinguishes it from other crystalline materials.

TABLE I

| Most Significant Lines of ZSM-22 | |
|---|---|
| Interplanar d-spacings (A) | Relative Intensity |
| 10.9 ± 0.2 | M-VS |
| 8.7 ± 0.16 | W |
| 6.94 ± 0.10 | W-M |
| 5.40 ± 0.08 | W |
| 4.58 ± 0.07 | W |
| 4.36 ± 0.07 | VS |
| 3.68 ± 0.05 | VS |
| 3.62 ± 0.05 | S-VS |
| 3.47 ± 0.04 | M-S |
| 3.30 ± 0.04 | W |
| 2.74 ± 0.02 | W |
| 2.52 ± 0.02 | W |

These values were determined by standard techniques. The radiation was the K-alpha doublet of copper and a diffractometer equipped with a scintillation counter and an associated computer were used. The peak heights, I, and the positions as a function of 2 theta, where theta is the Bragg angle, were determined using algorithms on the computer associated with the spectrometer. From these, the relative intensities, $100I/I_o$, where $I_o$ is the intensity of the strongest line or peak, and d (obs.) the interplanar spacing in angstroms (A), corresponding to the recorded lines, were determined.

In Table I, the relative intensities are given in terms of the symbols vs=very strong, s=strong, m=medium, w=weak, etc. It should be understood that this X-ray diffraction pattern is characteristic of all the species of ZSM-22 zeolite compositions. Ion exchange of the alkali or alkaline earth metal cations with other ions results in a zeolite which reveals substantially the same X-ray diffraction pattern as that of Table I with some minor shifts in interplanar spacing and variations in relative intensity. Other minor variations can occur, depending on the silica to alumina ratio of the particular sample, as well as its degree of thermal treatment.

The ZSM-22 zeolite freely sorbs normal hexane and has a pore dimension greater than about 4 Angstroms. In addition, the structure of the zeolite must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although, in some instances, excessive puckering or pore blockage may render these zeolites ineffective. Twelve-membered rings do not generally appear to offer sufficient constraint to produce the advantageous hydrocarbon conversions, although puckered structures exist such as TMA offretite which is a known effective zeolite. Also, such twelve-membered structures can be conceived that may be operative due to pore blockage or other causes.

Rather than attempt to judge from crystal structure whether or not a zeolite possesses the necessary constrained access, a simple determination of the "constraint index" may be made by passing continuously a mixture of an equal weight or normal hexane and 3-methylpentane over a sample of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000° F. for at least 15 minutes. The zeolite is then flushed with helium and the temperature adjusted between 550° F. (288° C.) and 950° F. (510° C.) to give an overall conversion between 10% and 60%. The mixture of hydrocarbons is passed at a 1 liquid hourly space velocity (LHSV), i.e., 1 volume of liquid hydrocarbon per volume of zeolite per hour, over the zeolite with a helium dilution to give a helium to total hydrocarbon mole ratio of 4:1. After 20 minutes on stream, a sample of the effluent is taken and analyzed, mmost conveniently by gas chromatography, to determine the fraction remaining unchanged for each of the two hydrocarbons.

While the above experimental procedure will enable one to achieve the desired overall conversion of 10 to 60% for most catalyst samples and represents preferred conditions, it may occasionally be necessary to use somewhat more severe conditions for samples of very low activity, such as those having a very high silica to alumina mole ratio. In those instances, a temperature of up to about 1000° F. and a liquid hourly space velocity of less than one, such as 0.1 or less, can be employed in order to achieve a minimum total conversion of about 10%.

Preliminary data indicates that the ZSM-22 zeolite has an orthorhombic noncentral structure consisting substantially of 5 and 6-member rings which form a substantially unidirectional 10-ring channel system. Four member rings appear to be completely absent from the structure, which may explain, at least to some extent, the relatively high thermal stability of ZSM-22. (A sample of ZSM-22 was found to be thermally stable after heating at 550° C. in air for 20 hours, and substantially steam stable, after the treatment at 920° F.—about 493° C.—for 5 hours in 1 atm saturated steam.) The ZSM-22 crystalline structure appears to be similar to zeolites of the ZSM-5 family, particularly ZSM-5, ZSM-11, ZSM-23, and ZSM-35. Accordingly, its performance characteristic may be similar to those of the aforementioned zeolites of the ZSM-5 family. Preliminary data, however, does not completely support this hypothesis. For example, the $\alpha$ activity, set forth in Table II, of ZSM-22 samples is less than that predicted for the ZSM-5 zeolite of equivlent $SiO_2/Al_2O_3$ ratios. Without wishing to be bound by any theory of operability, it is possible that trace amounts of the potassium cation ($K^+$) strategically located within the unidimensional channels may account for the reduced activity of the zeolite. Extractions of ZSM-22 samples with hydrochloric acid (HCl) to reduce the $K^+$ level in the zeolite may be effective in improving $\alpha$ activity.

TABLE II

Comparison of Activities for ZSM-22 and ZSM-5

| Form | Wt % K Present | $\alpha$-value Observed | (expected) |
|---|---|---|---|
| As-synthesized | 2.3 | — | (—) |
| TMA-exchanged[a] | 0.41 | 35 | ($\alpha$ = 130)[c] |
| NH$_4$-exchanged[b] | 0.04 | 61 | ($\alpha$ = 130)[c] |

[a]98° C., stirred 6 hrs. in 0.5 $\underline{N}$ tetramethyl ammonium bromide (TMABr).
[b]98° C., stirred 6 hrs. in 1.0 $\underline{N}$ NH$_4$NO$_3$.
[c]-value expected for ZSM-5 of equivalent $SiO_2/Al_2O_3$ ratio.

The alpha-test ($\alpha$-test) is an indication of the relative catalytic cracking activity of the catalyst compared to a standard catalyst. The value of $\alpha$ is the relative rate constant (rate of n-hexane conversion per unit volume of catalyst per unit time). It is based on the activity of highly active silica-alumina cracking catalyst taken as $\alpha=1$.

The $\alpha$-test is further described in a letter to the editor, entitled "Superactive Crystalline Alumino-Silicate Hydrocarbon Cracking Catalysts", by P. B. Weisz and J. N. Miale, *Journal of Catalysis*, Vol. 4, pp. 527–529 (August 1965) and in U.S. Pat. No. 3,354,078, the entire contents of both of which are incorporated herein by reference.

The sorption of hydrocarbons by ZSM-22 has also been surveyed and the results are summarized in Table III. Sorption capacities for n-hexane (normal hexane), cyclohexane, and water are about 4% by weight, or about one third that of ZSM-5. Without wishing to be bound by any theory of operability, it is thought that the reduced sorption capacity may be due to the unidimensional channel system of ZSM-22, but residual $K^+$ within the channels may also contribute to the relatively low sorption capacities. Cyclohexane and o-xylene sorption is relatively slow, making it difficult to determine equilibrium capacities.

TABLE III

ZSM-22 Sorption Data

| Sample | Form | n-hexane | 3-methyl-pentane | Cyclo-hexane[c] | $H_2O$ | o-xylene[b] |
|---|---|---|---|---|---|---|
| | | Sorptions (wt %)[a] | | | | |
| 1 | Hydrogen (H) | 3.9 | — | 2.8 | — | — |
| 2 | H | 4.2 | 3.9 | 1.1 | — | 2 |
| 3 | H | 4.1 | — | 3.3 | 4.7 | — |
| 4 | as-synthesized | 3.7 | — | 0.6 | 5.0 | — |

[a]Hydrocarbons: pressure = 20 mm, temperature = 25° C.; water-pressure = 12 mm, temperature = 25° C.
[b]pressure = 3.7 mm, temperature = 120° C.
[c]slow tailing sorption, nonequilibrium values.

Preliminary results also indicate that ZSM-22 is paraselective in its catalytic reactions. The ZSM-22 zeolite, as synthesized, tends to crystallize as agglomerates of elongate crystals having the size of about 0.5 to about 2.0 microns ($\mu$). Ballmilling fractures these crystals into smaller size crystallites (about 0.1$\mu$) without significant loss of crystallinity. The zeolite can be shaped into a wide variety of particle sizes. Generally speaking, the particles can be in the form of a powder, a granule, or a molded product, such as an extrudate having particle size sufficient to pass through a 2 mesh (Tyler) screen and be retained on a 400 mesh (Tyler) screen. In cases where the catalyst is molded, such as by extrusion, the crystals can be extruded before drying or partially dried and then extruded.

The as-synthesized ZSM-22 zeolite may be conveniently converted into the hydrogen, the univalent or multivalent cationic forms by base exchanging the zeolite to remove the alkali cations by such ions as hydrogen (from acids), ammonium, alkylammonium and arylammonium including $RNH_3$, $R_3NH^+$, $R_2NH_2^+$ and $R_4N^+$ where R is alkyl or aryl, provided the steric hindrance does not prevent the cations from entering the cage and cavity structure of the ZSM-22 type crystalline zeolite. The hydrogen form of the zeolite is prepared, for example, by base exchanging the alkali form with, e.g., ammonium chloride or hydroxide, whereby the ammonium ion is substituted for the sodium ion. The composition is then calcined, at a temperature of, e.g., 1000° F. (about 540° C.), causing evolution of ammonia and retention of the hydrogen proton in the composition.

Zeolite ZSM-23 is described in U.S. Pat. Nos. 4,076,842 and 4,104,151. Each of these patents is incorporated herein by reference.

Various methods may be employed in order to produce the catalyst of this invention. In the preparation the metallic hydrogenation/dehydrogenation component can be deposited on an alumina support and then admixed with the ZSM-22 or ZSM-23 zeolite. Alternatively the ZSM-22 or ZSM-23 zeolite can be composited with the alumina support and then exchanged or impregnated with the desired metal component. The composition or the catalyst of this invention may be varied, but broadly may be given as within the following limits. All values are expressed in percentages by weight.

| | Broad | Preferred |
|---|---|---|
| Metal in Elemental Form | 0.1–1 | .1–.6 |
| Alumina | 5–97 | 30–95 |
| ZSM-22 or ZSM-23 Zeolite | 3–80 | 5–70 |
| Additional Binder or Diluent | 0–20 | 0 |

Process Conditions

The use of our catalyst is preferred to be in a fixed bed. The feedstream to the process ordinarily will comprise a stream of a mixture of xylenes and ethylbenzene with traces of other hydrocarbons such as paraffins and other nonaromatics.

Ordinarily the catalyst will be contacted with the feedstream at a weight hourly space velocity of 0.5 to 15, preferably 1–7, based on the catalyst, operating pressures will range from between 0 to 1000 psig and preferably between 100 and 500 psig. Temperatures will be between 600° F. and 900° F., preferably between 750° F. and 850° F.

EXAMPLES

Example 1

This is an example of the preparation of the catalysts of this invention. A zeolite material was prepared in the lab which according to its X-ray diffraction analysis indicated it to be zeolite ZSM-22.

This zeolite was mixed with alpha alumina to make a mixture of 65 parts by weight of zeolite and 35 parts by weight of alumina. Sufficient water was added to the mixture so that the resulting catalyst could be formed into 1/16" extrudates. These extrudates were then calcined in a nitrogen atmosphere at 1000° F. Subsequently the calcined extrudate was contacted with a 1.0N ammonium nitrate solution and then calcined in air at 1000° F. The catalyst when tested had an alpha value of about 60. The extrudate was then contacted with an aqueous solution of chloroplatinic acid to produce a finished catalyst having a platinum content of 0.57% by weight. The catalyst was then calcined at 900° F. for 3 hours. The alpha value of the resulting catalyst was about 70. The catalyst composition was then contacted with a feedstream containing a mixture of toluene, ethylbenzene, para- meta- and orthoxylene in the percentages shown in Table IV. The results of these tests are shown in Examples 1 through 5 in Table IV.

Example 2

In a similar test the catalyst described in Example 10 of U.S. Pat. No. 4,128,591 was tested. The feedstock had a composition of about 30 percent ethylbenzene and 70 percent metaxylene. The results from this test are tabulated in Table IV as Example 10.

The catalyst properties of the catalyst described above are compared in Table IV to the best catalyst set forth in U.S. Pat. No. 4,128,591. The catalyst activity is measured by the ethylbenzene conversion and paraxylene equilibrium approach, while the selectivity is best measured by the $C_8$ ring retention. It is easily seen from Table IV that the present catalyst is both more active and selective than the platinum-mordenite catalyst even though the hydrogen to hydrocarbon ratio is lower (i.e., 3 vs. 8) and the ethylbenzene content is higher (i.e., 40 vs. 30%) for the present application. For example, at 800° F., the $C_8$ ring retention for the platinum HZSM-22 catalyst is greater than 90 percent with the paraxylene equilibrium approach greater than 94 percent, while that for the platinum mordenite composition is approximately 88 percent with the paraxylene equilibrium approach being 92 percent. The selectivity of xylene formation for the platinum-HZSM-22 catalyst is also superior to the platinum HZSM-5 catalyst of Table VIII. The platinum HZSM-5 zeolite catalyst was made of HZSM-5 zeolite steamed to an alpha value of about 5. Platinum was deposited on the zeolite to a concentration of 0.05%. The finished catalyst contained 65% of the metallized steam zeolite and 35% alumina.

Additional tests were made showing the effectiveness of ZSM-22 and ZSM-23 as catalysts.

Table V shows the effect of temperature on the process of this invention utilizing a catalyst containing 65 parts by weight of ZSM-22 zeolite and 35 parts of alumina and containing an overall concentration of 0.5% by weight of platinum.

Table VI shows the effect of space velocity on the process of this invention using the catalyst of the composition described above.

Table VII shows the effect of pressure on the process of this invention using the catalyst of the composition described above.

Table VIII shows the effect of utilizing a composition of 65 parts of zeolite HZSM-22 and 35 parts alumina, containing 0.6% by weight of platinum, a second composition of 65 parts of zeolite HZSM-23 zeolite and 35 parts alumina and 0.06% platinum; and a third composition of 65% HZSM-5 zeolite, 35% alumina and 0.05% of platinum.

The HZSM-23 catalyst, containing 65% zeolite and 35% alumina by weight was steamed to an alpha value of about 10. The catalyst was then contacted with an aqueous solution of chloroplatinic acid to produce a metals loading of 0.06% platinum. The catalyst was then calcined in air at 900° F. for 3 hours.

Table IX shows the effect of $C_8$ naphthene concentrations on catalysts consisting of 65% HZSM-23 zeolite, 35% alumina and 0.06% Pt utilizing feeds of 2 different compositions.

Table X shows the effect of both $C_7$ and $C_8$ naphthene on the process utilizing the catalyst of Table IX as well as a catalyst consisting of 65% HZSM-22 by weight and 35% alumina and 0.6% platinum.

Table XI shows the effect of ethylbenzene content on the process.

TABLE IV

CATALYTIC PROPERTIES OF Pt/HZSM-22 FOR XYLENE ISOMERIZATION

| Example No. | 1* | 2* | 3* | 4* | 5* | 10** |
|---|---|---|---|---|---|---|
| Catalyst: | 0.6% Pt/HZSM-22 | | | | | PT/Mordenite ($SiO_2Al_2O_3$ = 14.4/1) |
| Temp. °F. | 800 | 850 | 800 | 800 | 775 | 825 |
| Pressure, psig | | | 200 | | | 200 |
| H2/HC | | | 3 | | | 8 |
| WHSV | | 3.1 | | 1.6 | | 3 |
| Time on Stream, Hrs. | 13 | 26 | 38 | 51 | 242 | — |
| EB Conversion | 30 | 32 | 30 | 37 | 35 | — |
| P—Xylene Equl'm. App. % | 96 | 98 | 94 | 101 | 102 | 92 |
| Xylene Gain, Wt. % | 1.5 | −1.0 | 1.5 | 1.5 | 2.5 | — |
| $C_8$ Ring Retention, Mol. % | 98 | 91 | 96 | 94 | 95 | 88 |
| $C_9+$ Aromatics, Wt. % | 1.0 | 1.2 | 1.0 | 1.2 | 0.9 | — |
| BZ/EB, Mol Ratio | 0.3 | 0.6 | 0.4 | 0.3 | 0.2 | — |

*Xylene Feed Composition: Toluene 1.1%, Ethylbenzene 38.2%, Para-xylene 6.1%, Meta-xylene 41.4% and Ortho-xylene 13.2%
**U.S. Pat. 4,128,591 - Example 10 Xylene Feed: About 30% ethylbenzene, 70% meta-xylene

TABLE V

XYLENE ISOMERIZATION: EFFECT OF TEMPERATURE

| Catalyst: | 0.5% Pt/HZSM-22 | | | |
|---|---|---|---|---|
| Run No. CT-275- | 19.11 | 19.1 | 19.2 | 19.3 |
| TEMPERATURE, °F. | 775 | 800 | 850 | 900 |
| Pressure, psig | 200 | 200 | 200 | 200 |
| WHSV | 2.9 | 3.1 | 3.0 | 3.2 |
| H2/HC Molar Ratio | 2.8 | 2.6 | 2.7 | 2.5 |
| Time on Stream, Hrs | 254.0 | 13.0 | 26.0 | 32.0 |
| EB Conversion, Wt % | 26.1 | 30.3 | 32.3 | 46.6 |
| Xylene Gain, Wt %* | 0.8 | 1.5 | −1.0 | −2.8 |
| Arom Ring Loss, M % | 6.6 | 4.5 | 2.7 | 0.5 |
| P—Xylene, Equilibrium % | 91.6 | 95.8 | 98.1 | 100.5 |
| Prod Dist, Wt % | FEED | | | |
| C1-C4 N.A. | | 1.0 | 1.5 | 2.5 | 3.8 |
| C5-C7 N.A. | | 3.0 | 3.1 | 1.9 | 1.1 |
| C8 Naphthene | | 3.7 | 1.3 | 0.6 | 0.0 |
| C9 Naphthene | | | | | |
| Benzene | 0.0 | 1.3 | 2.2 | 5.0 | 10.4 |
| Toluene | 0.7 | 1.2 | 2.7 | 2.8 | 3.8 |
| EB | 38.1 | 27.9 | 26.4 | 25.7 | 20.2 |
| P—Xylene | 6.1 | 13.7 | 14.2 | 14.0 | 13.8 |
| M—Xylene | 40.7 | 34.4 | 34.1 | 32.7 | 31.4 |
| O—Xylene | 14.5 | 13.2 | 13.7 | 13.8 | 14.1 |
| C9+ Arom. | | 0.6 | 1.0 | 1.2 | 1.3 |
| Total | 100.0 | 100.0 | 100.0 | 100.0 | 100.0 |

TABLE VI

XYLENE ISOMERIZATION: EFFECT OF SPACE VELOCITY

| Catalyst: | 0.5% Pt/HZSM-22 | | | | |
|---|---|---|---|---|---|
| Run No. CT-275- | 19.5 | 19.4 | 19.6 | 19.10 | 19.11 |
| TEMPERATURE, °F. | 800 | 800 | 800 | 775 | 775 |
| Pressure, psig | 200 | 200 | 200 | 200 | 200 |
| WHSV | 1.6 | 3.0 | 4.2 | 1.7 | 2.9 |
| H2/HC Molar Ratio | 2.6 | 2.7 | 3.0 | 2.5 | 2.8 |
| Time on Stream, Hrs | 51.0 | 38.0 | 63.5 | 242.0 | 254.0 |
| EB Conversion, Wt % | 37.4 | 30.1 | 23.5 | 34.6 | 26.1 |
| Xylene Gain, Wt %* | 1.5 | 1.5 | −1.7 | 2.5 | 0.8 |
| P—Xylene, Equilibrium % | 100.9 | 94.3 | 87.0 | 102.2 | 91.6 |

TABLE VI-continued

XYLENE ISOMERIZATION: EFFECT OF SPACE VELOCITY

Catalyst: 0.5% Pt/HZSM-22

| Prod Dist, Wt % | FEED | | | | | |
|---|---|---|---|---|---|---|
| C1-C4 N.A. | | 3.0 | 1.5 | 1.3 | 1.9 | 1.0 |
| C5-C7 N.A. | | 3.8 | 2.6 | 2.3 | 4.2 | 3.0 |
| C8 Naphthene | | 1.0 | 1.2 | 1.3 | 2.3 | 3.7 |
| C9 Naphthene | | | | | | |
| Benzene | 0.0 | 3.2 | 3.0 | 1.9 | 1.7 | 1.3 |
| Toluene | 0.7 | 2.1 | 2.2 | 1.8 | 1.9 | 1.2 |
| EB | 38.1 | 23.7 | 26.5 | 29.0 | 24.7 | 27.9 |
| P—Xylene | 6.1 | 14.6 | 14.0 | 13.0 | 14.8 | 13.7 |
| M—Xylene | 40.7 | 33.2 | 34.1 | 33.9 | 33.7 | 34.4 |
| O—Xylene | 14.5 | 14.1 | 13.8 | 13.0 | 13.8 | 13.2 |
| C9+ Arom. | | 1.2 | 1.0 | 2.5 | 0.9 | 0.6 |
| Total | 100.0 | 100.0 | 100.0 | 100.0 | 100.0 | 100.0 |

TABLE VII

XYLENE ISOMERIZATION: EFFECT OF PRESSURE

CATALYST: 0.6% Pt/HZSM-22

| | | |
|---|---|---|
| Run No. CT-275- | 19.1 | 19.12 |
| TEMPERATURE, °F. | 800 | 800 |
| Pressure, psig | 200 | 300 |
| WHSV | 3.1 | 3.1 |
| H2/HC Molar Ratio | 2.6 | 2.6 |
| Time on Stream, Hrs | 13.0 | 261.0 |
| EB Conversion, Wt % | 30.3 | 45.1 |
| Xylene Gain, Wt %* | 1.5 | 3.7 |
| P—Xylene, Equilibrium % | 95.8 | 104.2 |
| Prod Dist, Wt % | FEED | |
| C1-C4 N.A. | 1.5 | 1.5 |
| C5-C7 N.A. | 3.1 | 5.9 |
| C8 Naphthene | 1.3 | 5.7 |
| C9 Naphthene | | |
| Benzene | 0.0 | 2.2 | 1.3 |
| Toluene | 0.7 | 2.7 | 1.2 |
| EB | 38.1 | 26.4 | 20.7 |
| P—Xylene | 6.1 | 14.2 | 15.1 |
| M—Xylene | 40.7 | 34.1 | 33.9 |
| O—Xylene | 14.5 | 13.7 | 13.9 |
| C9+ Arom. | | 1.0 | 0.8 |
| Total | 100.0 | 100.0 | 100.0 |

TABLE VIII

XYLENE ISOMERIZATION: EFFECT OF ZEOLITE

| Catalyst: | | 0.6% Pt/HZSM-22 60 | 0.05% Pt/HZSM-23 10 | | 0.05% Pt/HZSM-5 5 |
|---|---|---|---|---|---|
| Run No. CT-275- | | 19.1 | 22.1 | | 23.1 |
| TEMPERATURE, °F. | | 800 | 800 | | 794 |
| Pressure, psig | | 200 | 200 | | 200 |
| WHSV | | 3.1 | 3.0 | | 5.8 |
| H2/HC Molar Ratio | | 2.6 | 2.8 | | 2.9 |
| Time on Stream, Hrs | | 13.0 | 20.0 | | 11.5 |
| EB Conversion, Wt % | | 30.3 | 46.7 | | 62.6 |
| Xylene Gain, Wt %* | | 1.5 | 1.6 | | 1.3 |
| P—Xylene, Equilibrium % | | 95.8 | 103.8 | | 104.0 |
| Prod Dist, Wt % | FEED | | | | |
| C1-C4 N.A. | | 1.5 | 2.9 | | 5.7 |
| C5-C7 N.A. | | 3.1 | 4.9 | | 1.5 |
| C8 Naphthene | | 1.3 | 1.4 | | 0.6 |
| C9 Naphthene | | | | | |
| Benzene | 0.0 | 2.2 | 5.2 | | 12.7 |
| Toluene | 0.7 | 2.7 | 1.4 | 1.1 | 2.0 |
| EB | 38.1 | 26.4 | 20.1 | 40.0 | 14.5 |
| P—Xylene | 6.1 | 14.2 | 14.8 | 6.1 | 14.5 |
| M—Xylene | 40.7 | 34.1 | 32.3 | 40.1 | 31.3 |
| O—Xylene | 14.5 | 13.7 | 14.8 | 13.7 | 14.5 |
| C9+ Arom. | | 1.0 | 2.3 | | 2.6 |
| Total | 100.0 | 100.0 | 100.0 | 100.0 | 100.0 |

TABLE IX

XYLENE ISOMERIZATION: EFFECT OF C8 NAPHTHENE

CATALYST: .05% Pt/HZSM-23 (10)

| | | | | |
|---|---|---|---|---|
| Run No. CT-275- | 25.1 | 25.2 | 25.4 | 25.5 |
| TEMPERATURE, °F. | 800 | 804 | 800 | 800 |
| Pressure, psig | 200 | 300 | 200 | 200 |
| WHSV | 3.0 | 5.9 | 2.8 | 5.8 |
| H2/HC Molar Ratio | 2.8 | 2.8 | 3.0 | 2.9 |
| Time on Stream, Hrs | 14.5 | 27.5 | 62.5 | 74.5 |
| EB Conversion, Wt % | 48.0 | 46.9 | 42.6 | 25.5 |
| Xylene Gain, Wt % | 3.7 | 3.1 | 5.6 | 5.5 |
| P—Xylene, Equilibrium % | 106.4 | 105.0 | 104.7 | 102.0 |
| Prod Dist, Wt % | FEED | | | |
| C1-C4 N.A. | 4.5 | 3.9 | 5.4 | 3.1 |
| C5-C7 N.A. | 6.7 | 8.9 | 5.8 | 4.0 |

TABLE IX-continued
XYLENE ISOMERIZATION: EFFECT OF C8 NAPHTHENE

| CATALYST: | .05% Pt/HZSM-23 (10) | | | | | |
|---|---|---|---|---|---|---|
| C8 Naphthene | 5.1 | 1.2 | 1.7 | 9.6 | 1.3 | 2.4 |
| C9 Naphthene | | 0.2 | 0.4 | | | |
| Benzene | | 6.2 | 4.4 | | 6.9 | 4.5 |
| Toluene | 1.0 | 1.4 | 1.2 | 0.9 | 1.2 | 1.1 |
| EB | 37.2 | 19.3 | 19.7 | 35.3 | 20.2 | 26.3 |
| P—Xylene | 5.7 | 14.2 | 14.0 | 5.4 | 13.7 | 13.5 |
| M—Xylene | 38.0 | 30.4 | 30.2 | 36.3 | 29.6 | 29.7 |
| O—Xylene | 12.9 | 13.8 | 13.7 | 12.3 | 13.6 | 13.8 |
| C9+ Arom. | | 2.3 | 2.0 | 2.5 | 2.2 | 1.7 |
| Total | 99.9 | 100.0 | 100.0 | 100.0 | 100.0 | 100.0 |

TABLE X
XYLENE ISOMERIZATION: EFFECT OF C7 AND C8 NAPHTHENE

| CATALYST: | 0.05% Pt/HZSM-23 (10) | | | 0.6% Pt/HZSM-22 (60) | | |
|---|---|---|---|---|---|---|
| Run No. CT-275- | | 25.4 | 26.1 | | 26.2 | 26.3 |
| TEMPERATURE, °F. | | 800 | 800 | | 800 | 800 |
| Pressure, psig | | 200 | 200 | | 200 | 300 |
| WHSV | | 2.8 | 2.7 | | 2.8 | 2.9 |
| H2/HC Molar Ratio | | 3.0 | 3.1 | | 3.1 | 3.0 |
| Time on Stream, Hrs | | 62.5 | 4.0 | | 11.0 | 16.0 |
| EB Conversion, Wt % | | 42.6 | 35.6 | | 31.1 | 55.2 |
| Xylene Gain, Wt % | | 5.6 | 11.9 | | 14.6 | 18.4 |
| P—Xylene, Equilibrium % | | 104.7 | 101.4 | | 103.4 | 110.0 |
| Prod Dist, Wt % | FEED | | | | | |
| C1-C4 N.A. | | 5.4 | 3.2 | | 2.6 | 2.7 |
| C5-C7 N.A. | | 5.8 | 4.5 | 2.3 | 4.7 | 8.7 |
| C8 Naphthene | 9.6 | 1.3 | 2.3 | 9.8 | 2.5 | 5.8 |
| C9 Naphthene | | | | | | |
| Benzene | | 6.9 | 2.5 | | 2.3 | 1.6 |
| Toluene | 0.9 | 1.2 | 3.3 | 0.9 | 3.2 | 3.1 |
| EB | 35.3 | 20.2 | 22.7 | 34.6 | 23.8 | 15.5 |
| P—Xylene | 5.4 | 13.7 | 14.3 | 5.3 | 14.3 | 15.3 |
| M—Xylene | 36.3 | 29.6 | 31.9 | 35.1 | 31.5 | 32.0 |
| O—Xylene | 12.3 | 13.6 | 14.3 | 11.9 | 14.2 | 14.5 |
| C9+ Arom. | | 2.2 | 1.0 | | 0.8 | 0.8 |
| Total | 100.0 | 100.0 | 100.0 | 100.0 | 100.0 | 100.0 |

TABLE XI
XYLENE ISOMERIZATION: EFFECT OF ED CONTENT

| CATALYST | | | | CATALYST 0.6% Pt/HZSM-22 | | | | | |
|---|---|---|---|---|---|---|---|---|---|
| Run No. CT-275- | | 19.1 | 19.1 | 26.8 | 26.9 | | 26.1 | 26.1 | |
| TEMPERATURE, °F. | | 800 | 800 | 800 | 800 | | 800 | 800 | |
| Pressure, psig | | 200 | 300 | 200 | 300 | | 200 | 300 | |
| WHSV | | 3.1 | 3.1 | 2.8 | 2.8 | | 2.8 | 2.8 | |
| H2/HC Molar Ratio | | 2.6 | 2.6 | 1.5 | 1.5 | | 1.5 | 1.5 | |
| Time on Stream, Hrs | | 13.0 | 261.0 | 76.0 | 88.5 | | 93.5 | 105.0 | |
| EB Conversion, Wt % | | 30.3 | 45.1 | 30.1 | 42.6 | | 25.0 | 41.7 | |
| Xylene Gain, Wt % | | 1.5 | 3.7 | 1.1 | 3.1 | | −0.9 | 0.1 | |
| P—Xylene, Equilibrium % | | 95.8 | 104.2 | 99.4 | 105.8 | | 97.9 | 105.8 | |
| Prod Dist, Wt % | FEED | | | | | | | | |
| C1-C4 N.A. | | 1.5 | 1.5 | 1.7 | 1.3 | | 0.8 | 1.2 | |
| C5-C7 N.A. | | 3.1 | 5.9 | 2.4 | 4.4 | | 2.2 | 4.6 | |
| C8 Napthene | | 1.3 | 5.7 | 1.3 | 2.9 | | 1.0 | 2.9 | |
| C9 Napthene | | | | | | | | | |
| Benzene | 0.0 | 2.2 | 1.3 | 0.0 | 2.3 | 1.7 | 2.1 | 1.4 | |
| Toluene | 0.7 | 2.7 | 1.2 | 1.3 | 1.8 | 1.8 | 1.4 | 1.9 | 1.9 |
| EB | 38.1 | 26.4 | 20.7 | 30.8 | 21.4 | 17.6 | 25.7 | 19.3 | 14.9 |
| P—Xylene | 6.1 | 14.2 | 15.1 | 6.9 | 15.9 | 16.8 | 7.5 | 16.7 | 17.5 |
| M—Xylene | 40.7 | 34.1 | 33.9 | 45.5 | 37.3 | 37.3 | 49.0 | 39.5 | 38.7 |
| O—Xylene | 14.5 | 13.7 | 13.9 | 15.3 | 15.1 | 15.5 | 16.4 | 15.9 | 16.2 |
| C9+ Arom. | | 1.0 | 0.8 | | 0.8 | 0.8 | | 0.7 | 0.7 |
| Total | 100.0 | 100.0 | 100.0 | 100.0 | 100.0 | 100.0 | 100.0 | 100.0 | 100.0 |

What is claimed is:

1. A process for producing a near equilibrium mixture of xylenes from a feed comprising ethylbenzene and mixed xylenes which comprises contacting the feed with hydrogen in the presence of a catalyst composition consisting essentially of 0.1 to 1 weight percent of a hydrogenation/dehydrogenation metal, 5 to 97 weight percent alumina and 3 to 80 weight percent ZSM-23 zeolite
   wherein catalyst contact with the feed is undertaken at a weight hourly space velocity of 0.5 to 15 based on the catalyst, a pressure of from between 0 to 1000 psig and a temperature of from between 600° F. and 900° F., and wherein ZSM-23 is steamed prior to hydrogenation/dehydrogenation metal incorporation into the catalyst composition.

2. The process of claim 1 wherein said metal of (a) is selected from the group consisting of platinum, palladium, nickel, gold, zinc, gallium or rhenium and combinations of two or more thereof.

3. The process of claim 1 wherein said ZSM-23 zeolite is the hydrogen form.

4. The process of claim 1 wherein the ZSM-23 zeolite constitutes between about 30 and about 70 percent by weight of the total catalyst composition.

5. The process of claim 1 wherein the metal component constitutes between about 0.1 and about 0.6 percent by weight of the total composition.

6. The process of claim 1, wherein said hydrogenation/dehydrogenation is platinum.

* * * * *